(12) United States Patent
Alarcon-Lorca et al.

(10) Patent No.: US 6,613,929 B2
(45) Date of Patent: Sep. 2, 2003

(54) PROCESS FOR PREPARATION OF FLUOROFORMATES

(75) Inventors: Alphonse Alarcon-Lorca, Soisy sur Seine (FR); Thierry Malfroot, Saintry sur Seine (FR); Jean-Pierre Senet, Buthiers (FR)

(73) Assignee: Isochem (FR)

( * ) Notice: Subject to any disclaimer, the term of this patent is extended or adjusted under 35 U.S.C. 154(b) by 0 days.

(21) Appl. No.: 10/323,956

(22) Filed: Dec. 18, 2002

(65) Prior Publication Data

US 2003/0120103 A1 Jun. 26, 2003

(30) Foreign Application Priority Data

Dec. 20, 2001 (FR) .............................. 01 16514

(51) Int. Cl.$^7$ .......................... C07C 69/96; C07C 51/58
(52) U.S. Cl. ...................... 558/281; 558/282; 562/852
(58) Field of Search ............... 558/281, 282; 562/852

(56) References Cited

U.S. PATENT DOCUMENTS 3,362,980 A * 1/1968 Christe et al. .............. 260/463
3,696,150 A 10/1972 Lichstein et al. .......... 260/544

OTHER PUBLICATIONS

XP–002211567—1992 Suyama et al, pp. 93–99.
XP 000196864 Tullock et al, vol. 25, pp. 2016–2019 (1960).
XP002932758 pp. 2538–2541, 1980. J. Org. Chem.
XP–002211568, pp. 793–794. Ichihara et al (1986).
XP–002134146 J. Org.Chem. vol. 44, No. 6, 1979 pp.1016–1017.

* cited by examiner

Primary Examiner—Joseph K. McKane
Assistant Examiner—Ebenezer Sackey
(74) Attorney, Agent, or Firm—Muserlian, Lucas and Mercanti

(57) ABSTRACT

A process for the preparation of fluoroformates of the formula

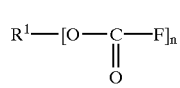

wherein $R^1$ is a saturated or unsaturated, substituted or unsubstituted and primary or secondary aliphatic, a saturated or unsaturated, substituted or unsubstituted secondary cycloaliphatic or a substituted or unsubstituted aromatic or heteroaromatic, and n is equal to 1, 2 or 3, comprising reacting a corresponding chloroformate of formula I with an alkali metal fluoride in ethylene carbonate at a temperature wherein the ethylene carbonate is liquid whereby it is possible to very rapidly obtain the fluoroformates with excellent yields and high purity.

6 Claims, No Drawings

PROCESS FOR PREPARATION OF FLUOROFORMATES

The present invention relates to an improved process for the preparation of fluoroformates. It relates in particular to the improved process for the preparation of fluoroformates by exchange of chlorine by fluorine in chloroformates.

STATE OF THE ART

Fluoroformates are known compounds and are very useful as intermediates in the synthesis of organic compounds employed in agriculture or in pharmaceuticals. They make possible particularly the introduction of oxycarbonylated radicals into molecules and advantageously replace chloroformates, which are often unstable under the reaction conditions used.

One of the known processes for the preparation of fluoroformates consists in reacting a carbonyl fluoride halide with an alcohol or a phenol, but this process exhibits several disadvantages. Carbonyl fluoride halides are very difficult to prepare and therefore are very uncommon and very expensive. As they cannot be stored, they have to be manufactured immediately before use. It is also difficult and dangerous to handle them since a special plant is necessary and very low temperatures are used. Furthermore, the sodium fluoride employed must have a specific particle size. The process is consequently not very economical.

Another preparation, described by J. Cuomo and R. A. Olofson (J. Org. Chem., vol. 44, No. 6, 1979), is carried out starting from chloroformates by exchange of the chlorine by fluorine. The reaction is carried out using potassium fluoride in the presence of a catalyst to activate it, such as the crown ether 18-C-6, which complexes the potassium. However, first, crown ethers are not common compounds and they are consequently sold at very high prices; secondly, the reaction times indicated are very high, from 45 hours to 73 hours for aliphatic fluoroformates, 144 hours for aromatic fluoroformates, such as phenyl fluoroformate.

Improvements to this process were then proposed by J. Ichihara et al. (J. Chem. Soc., Chem. Commun., 1986. pp. 793–4). They consist in using a calcined mixture of potassium fluoride and of calcium fluoride in a solvent such as acetonitrile. The reaction time for preparing ethyl fluoroformate is still very high, 24 hours. The calcined mixtures of fluorides have to be carefully prepared beforehand according to a specific procedure and at high temperature.

OBJECTS OF THE INVENTION

It is an object of the invention to obtain fluoroformates from the corresponding chloroformates under better conditions than those of the processes of the prior art and in particular with much shorter reaction times.

This and other objects and advantages of the invention will become obvious from the following detailed description.

THE INVENTION

According to the process of the invention, fluoroformates of the formula

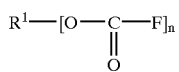

wherein $R_1$ is a saturated or unsaturated, substituted or unsubstituted and primary or secondary aliphatic, a saturate or unsaturated arid substituted or unsubstituted secondary cycloaliphatic or a substituted or unsubstituted aromatic or heteroaromatic ring, and n is equal to 1, 2 or 3, are prepared by reaction of the corresponding chloroformate of the formula

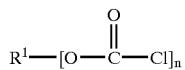

with an alkali metal fluoride in ethylene carbonate at a temperature wherein the ethylene carbonate is liquid.

The fluoroformates are very rapidly obtained on carrying out the process under these conditions. The reaction time is generally from 1 to 2 hours, both for aliphatic fluoroformates and for aromatic fluoroformates. Their yields and their purities are excellent and often markedly improve with respect to those of the prior art.

The chloroformates which are used as starting compounds are commercially available or are prepared according to the methods known per se.

The process of the invention is preferably carried out by adding the chloroformate to the mixture of the alkali metal fluoride and ethylene carbonate and for best results, this addition is carried out gradually.

The process of the invention is well suited to the preparation of fluoroformates for which the starting chloroformates are stable in highly polar media and are liquid at normal temperatures.

It is also particularly well suited when the fluoroformates which it is desired to obtain are liquid at normal temperature and when they have a markedly lower boiling point than that of ethylene carbonate.

The chloroformates of use are preferably primary and secondary aliphatic chloroformates, non-tertiary cycloaliphatic chloroformates, or aromatic or heteroaromatic chloroformates not carrying strong electron-withdrawing groups on the ring.

$R^1$ can represent preferably a primary or secondary aliphatic, more preferably a substituted or unsubstituted aliphatic of 2 to 10 carbon atoms, and most preferably, 2 to 8 carbon atoms.

Carbon-carbon double or triple bonds can be present, provided that the double or triple bond is not on the carbon in the 2 position, that is to say that it is not, for example, allyl or propargyl.

The aliphatic chain can be linear or branched and it can comprise heteroatoms, such as oxygen or sulfur atoms. The substituents can be selected in particular from halogenated or nonhalogenated cycloaliphatic or halogenated or nonhalogenated aromatic, provided that the latter are not attached to the carbon carrying the formate group, halogen atoms, provided that they are not attached to the carbon carrying the formate group, or halogenated or nonhalogenated alkoxy or aryloxy.

Mention may be made, as examples, ethyl, n-propyl, isopropyl, vinyl, isopropenyl, n-butyl or isobutyl or derived from the glycol. When $R^1$ is cycloaliphatic, the latter can be polycyclic. Preferably, the ring attached to the formate group contains 4 to 7 carbon atoms and it can be unsaturated, with the same restrictions as for the aliphatic.

The substituents on the aliphatic ring or rings can be selected from halogen, halogenated or nonhalogenated aliphatic, cycloaliphatic, aromatic, alkoxy or aryloxy. Examples include cycloaliphatic of cyclopentyl, cyclohexyl, adamantyl or cholesteryl.

$R^1$ can also be a mono- or polycyclic aromatic or heteroaromatic. The ring or rings can carry substituents selected particularly from halogen, halogenated or nonhalogenated aliphatic, cycloaliphatic, aromatic alkoxy or aryloxy, and the like. When the substituents are strong electron-withdrawing, they are generally less suitable.

Heteroaromatic radicals are in particular those in which the hetero ring has 5 or 6 ring members. The heteroatoms of the ring or rings are selected from nitrogen, sulfur or oxygen, preferably from oxygen or sulfur.

Mention may in particular be made, as aromatic, of the substituted or unsubstituted phenyl or naphthyl. As heteroaromatic radical mention may in particular be made of the substituted or unsubstituted furyl, pyrrolyl, thienyl, pyridlyl or pyrimidinyl. As halogen atoms, chlorine, bromine or fluorine are preferably chosen.

One, two or three formate groups can be attached to $R^1$. Examples are bisfluoroformate compound, of diethylene glycol bisfluoroformate.

The chlorine-fluorine exchange is carried out using alkali metal fluorides which are commercially available. They are generally used in powder form to accelerate their dissolution in the ethylene carbonate. The alkali metal is preferably sodium or potassium and more particularly potassium.

The amount of alkali metal fluoride with respect to the chloroformate is not critical. According to the stoichiometry of the reaction, it is desirable for at least one fluorine atom per chlorine atom to be replaced to be present in the reaction. Preferably, 1.2 to 2 molar equivalents of alkali metal fluoride with respect to the chloroformate are used.

To obtain the above-mentioned advantages, it is necessary for the reaction to take place in ethylene carbonate which is a compound which is solid at normal temperature. Due to its structure, it might be feared that it will easily decarboxylate or that it will react with the compounds present in the medium.

In point of fact, it has now been found that its use very markedly improves the reaction between the chloroformate and the alkali metal fluoride when it is used in the liquid state as solvent, that is to say when the reaction is carried out at a temperature equal to or greater than its melting point, which is in particular 37°–39° C. under the normal atmospheric pressure.

Furthermore, it is not necessary to accelerate the reaction, to use high temperatures, for example greater than 100° C., particularly for preparing aromatic fluoroformates. The reaction can be carried out at a temperature between the melting point of ethylene carbonate and approximately 60°. A temperature between 40° C. and 50° C. or equal to these values is preferably chosen.

The amount of ethylene carbonate is not a determining factor but it must be sufficient to allow good stirring of the medium. An excessive amount leads to a drop in productive output and very significant decomposition of the chloroformates. Use is generally made of 2.5 to 5 equivalents of ethylene carbonate.

For the implementation of the process, generally first the alkali metal fluoride and the ethylene carbonate are mixed. The chloroformate is subsequently added to the mixture formed and stirred. The addition to the mixture is preferably carried out gradually. The reaction can be carried out at atmospheric pressure and is preferably carried out under anhydrous conditions. The reaction time is considerably shorter than in the prior processes. Thus, for aliphatic and cycloaliphatic fluoroformates, the reaction time of the method used by J. Cuomo et al. was from 45 hours to 73 hours. By virtue of the invention, it is approximately 1 to 2 hours. Likewise, cyclohexyl fluoroformate was obtained previously in 4 hours at a temperature of 70° C. while with the invention, the product is obtained in scarcely one hour at a temperature of 45° C.

The fluoroformates obtained can be recovered by conventional methods. Generally, the volatile compounds are evaporated under reduced pressure by varying the temperature and the pressure in the reactor. The volatile compounds are collected in a receiver maintained at low temperature, such as on the order of −50° C. to −70° C. If necessary, a distillation is carried out to purify the fluoroformate.

The fluoroformate yields are excellent and generally improved with respect to those of the prior art. Phenyl fluoroformate, for example, was recovered by the prior art in 144 hours with a yield of only 80%; and with the invention is obtained in approximately two hours with a markedly better yield of 93.5%. The purity of the fluoroformates obtained is excellent and distillation is not always necessary.

In the following examples, there are described several preferred embodiments to illustrate the invention. However, it is to be understood that the invention is not limited to the preferred embodiments.

EXAMPLE 1

Preparation of Isopropyl Fluoroformate 8,938 g (106.4 mol) of ethylene carbonate were introduced into a fully equipped 20 liter glass reactor and were dried with stirring for 5 hours.at a temperature of 90° C. under a pressure of 80 mm Hg. The addition was then carried out of 3,306 g (57 mol) of powdered potassium fluoride dried beforehand at 100° C. under 1 mm Hg over 5 hours. The reactor was cooled and 4,655 g (38 mol) of isopropyl chloroformate were introduced, under nitrogen and at atmospheric pressure, over 2 hours into the reaction medium maintained between 40° and 45° C. The progress of the reaction was monitored by gas chromatography (GC).

It was found that the reaction was finished at the end of the introduction of the chloroformate and fluoroformate formed was recovered, in a receiver maintained at approximately −60° C., by evaporation under vacuum, the temperature in the reactor being varied from 50° to 82° C. and the pressure being varied from 760 to 35 mm Hg. It was purified by distillation under reduced pressure to obtain 3,750 g of isopropyl fluoroformate (93% yield). Its purity, determined by GC, was 99.9% and the level of hydrolyzable fluorine was 100%.

EXAMPLE 2

Preparation of N-octyl Flouroformate

The preparation was carried out as in Example 1 but using 100 g of ethylene carbonate, 30 g (0.52 mol) of potassium fluoride and 67.5 g (0.35 mol) of n-octyl chloroformate. After addition of the chloroformate, stirring of the reaction mixture was continued at 45° C. for 1.5 hours. Evaporation under vacuum was carried out at a temperature varying from 50° to 100° under a pressure from 760 to 10 mm Hg. By distillation under reduced pressure of the compounds collected, 54.9 (89% yield) of n-octyl fluoroformate were recovered with a boiling point of 87° C. at 14 mm Hg.

EXAMPLE 3

Preparation of Neopentyl Flouroformate

The preparation was carried out as in Example 2 but using 120 g of ethylene carbonate, 45 g (0.77 mol) of potassium fluoride and 75.3 g (0.5 mol) of neopentyl chloroformate. After addition of the chloroformate, stirring of the reaction mixture was continued for 1 hour at 45° C. Evaporation under vacuum was carried out as in the preceding example. By distillation under reduced pressure, 61.7 g (92% yield) of neopentyl fluoroformate were recovered with a boiling point of 60° C. at 20 mm Hg.

EXAMPLE 4

Preparation of Phenyl Fluoroformate

The preparation was carried out as in Example 2 but using 250 g of ethylene carbonate, 89 g (1.53 mol) of potassium fluoride and 156.6 g (1.0 mol) of phenyl chloroformate. After addition of the chloroformate, stirring of the reaction mixture was continued at 45°–50° C. for 2 hours. Evaporation under vacuum was carried out as above. By distillation under reduced pressure, 131 g (93.5% yield) of phenyl fluoroformate with a boiling point of 62°–64° at 40 mm Hg were recovered.

EXAMPLE 5

Preparation of Cyclohexyl Fluoroformate

The preparation was carried out as in Example 2 but using 250 g of ethylene carbonate, 90 g (1.55 mol) of potassium fluoride and 162.6 g (1.0 mol) of cyclohexyl chloroformate. After addition of the chloroformate, stirring of the mixture was continued for 45 minutes at 45° C. Evaporation under vacuum was carried out as above. By distillation under reduced pressure, 122.7 g (84% yield) of cyclohexyl fluoroformate with a boiling point of 55–56° C. at 22 mm Hg were obtained.

Various modifications of the process may be made without departing from the spirit or scope thereof and it is to be understood that the invention is intended to be limited only as defined in the appended claims.

What we claim is:

1. A process for the preparation of a fluoroformate of the formula

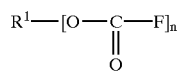

$$R^1-[O-\underset{\underset{O}{\|}}{C}-F]_n \quad \text{I}$$

wherein $R^1$ is selected from the group consisting of a saturated or unsaturated, substituted or unsubstituted and primary or secondary aliphatic, a saturated or unsaturated, substituted or unsubstituted secondary cycloaliphatic and a substituted or unsubstituted aromatic or heteroaromatic ring, and n is equal to 1, 2 or 3, comprising reacting the corresponding chloroformate of the formula

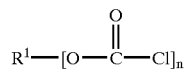

$$R^1-[O-\underset{\underset{O}{\|}}{C}-Cl]_n$$

with an alkali metal fluoride in etheylene carbonate at a temperature at which the ethylene carbonate is liquid.

2. The process of claim 1 wherein the chloroformate is introduced into the mixture of the alkali metal fluoride and ethylene carbonate.

3. The process of claim 2 wherein the introduction of the chloroformate is carried out gradually.

4. The process of claim 1 wherein the alkali metal fluoride is sodium fluoride or potassium fluoride.

5. The process of claim 1 wherein the alkali metal fluoride is in powder form.

6. The process of claim 1 wherein the reaction temperature is between the melting point of ethylene carbonate and 60° C.

* * * * *